(12) United States Patent
Chakrabarti

(10) Patent No.: US 8,911,725 B2
(45) Date of Patent: Dec. 16, 2014

(54) CO-TARGETING OF AURORA A KINASE AND LIM KINASE 1 FOR CANCER THERAPY

(75) Inventor: Ratna Chakrabarti, Winter Springs, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 144 days.

(21) Appl. No.: 13/167,431

(22) Filed: Jun. 23, 2011

(65) Prior Publication Data

US 2012/0034236 A1    Feb. 9, 2012

Related U.S. Application Data

(60) Provisional application No. 61/357,652, filed on Jun. 23, 2010.

(51) Int. Cl.
  *A61K 39/395* (2006.01)
  *A61K 31/7088* (2006.01)
  *A61K 31/55* (2006.01)
  *G01N 33/574* (2006.01)

(52) U.S. Cl.
  CPC .............. *A61K 31/7088* (2013.01); *A61K 31/55* (2013.01); *G01N 33/57484* (2013.01); *G01N 2333/912* (2013.01); *G01N 2500/04* (2013.01); *G01N 2500/10* (2013.01)
  USPC ..................................... 424/130.1; 424/138.1

(58) Field of Classification Search
  None
  See application file for complete search history.

(56) References Cited

U.S. PATENT DOCUMENTS

| 2010/0120771 A1 | 5/2010 | Clark |
| 2010/0144783 A1 | 6/2010 | Michaelides |
| 2011/0251255 A1 | 10/2011 | Chakrabarti |

FOREIGN PATENT DOCUMENTS

WO    2010135662    11/2010

OTHER PUBLICATIONS

Seth et al., Ther. Deliv., 2012, vol. 3(2):245-261, see Abstract.*
Davila et al., Mol. Cancer, 2007, 6:40.*
Wu et al., Sichuan Da Xue Xue Bao Yi Xue Ban, 2007, vol. 38(2):306-308, see Abstract.*
Technical Bulletin #506, "Using siRNA for gene silencing is a rapidly evolving tool in molecular biology", 2013, http://www.lifetechnologies.com/us/en/home/references/ambion-tech-support/rnai-sirna/general-articles/-sirna-designguidelines.html.
MacDonald et al., "Identification of a nonkinase target mediating cytotoxicity of novel kinase inhibitors", Molecular Cancer Therapeutics, Nov. 2008, vol. 7, pp. 3490-3498.
Tuschl, T. et al, "The siRNA User Guide", Revised May 6, 2004, http://www.rockefeller.edu/labheads/tuschl/sirna.html.

* cited by examiner

*Primary Examiner* — Xiaozhen Xie
(74) *Attorney, Agent, or Firm* — Timothy H. Van Dyke; Beusse, Wolter, Sanks & Maire, P.A.

(57) ABSTRACT

Disclosed herein are therapies for treating or preventing reoccurrence of cancer. The therapies involved inhibition of LIMK1 in conjunction with AurKA inhibition. Specifically exemplified herein is the administration of an AurKA inhibitor in conjunction with a LIMK1 RNA interfering molecule.

4 Claims, 17 Drawing Sheets

Western blot analysis of the total cell extracts from $BPH^V$ or $BPHL^{CA}$ cells using anti-LIMK1 or anti-AurKA antibodies. GAPDH expression was used as the loading control. $BPHL^{CA}$: BPH-1 cells expressing Flag-tagged phosphomimic LIMK1 (constitutively active), $BPH^V$: BPH-1 cells transfected with the empty vector.

FIG. 2 LIMK1 Constructs
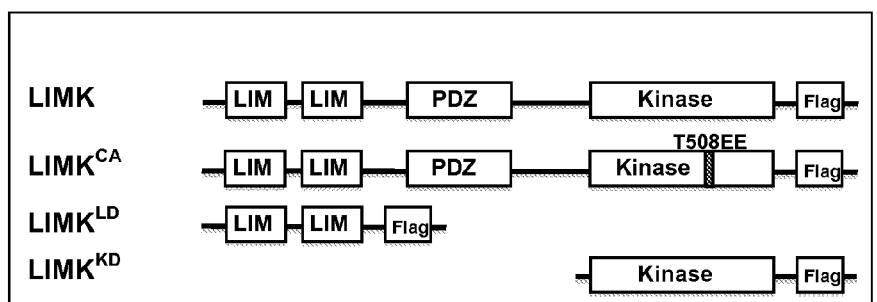
Full length (LIMK), constitutively active phosphomimic (LIMK$^{CA}$), LIM-domain only (LIMK$^{LD}$), and kinase-domain only (LIMK$^{KD}$) LIMK1 constructs were cloned into the pCMV14 vector used for expression in RWPE1 cells.

A: PC3 cells were transfected with either LIMK1 or control shRNA. In control shRNA transfected cells, distinct localization of pAurKA (green) at the spindle poles (red) could be noted. In LIMK1 shRNA treated cells, alpha-tubulin staining (red) showed disorganized spindle structure. Diffused

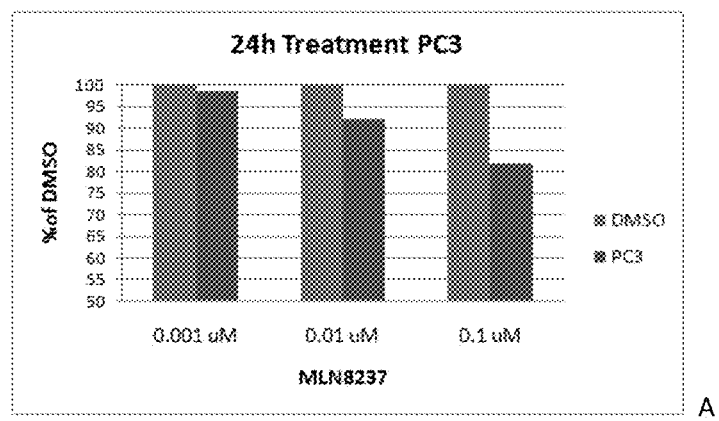
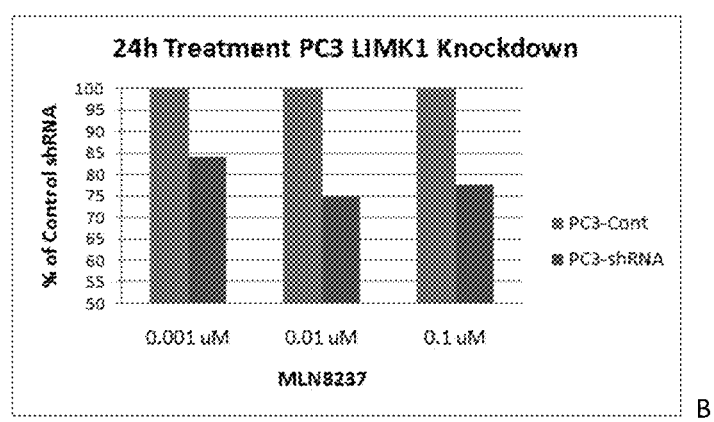
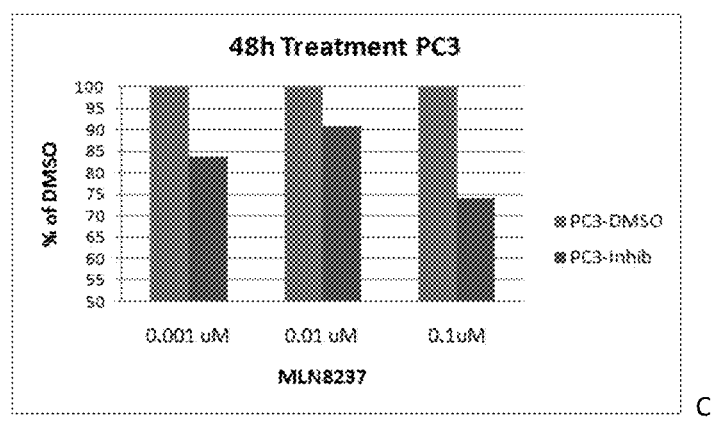
FIG. 9

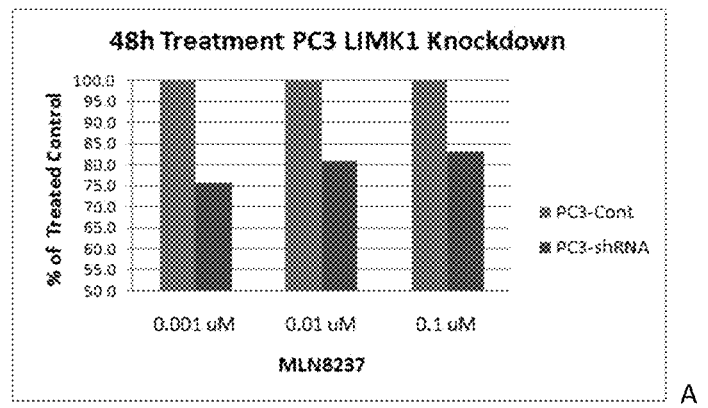
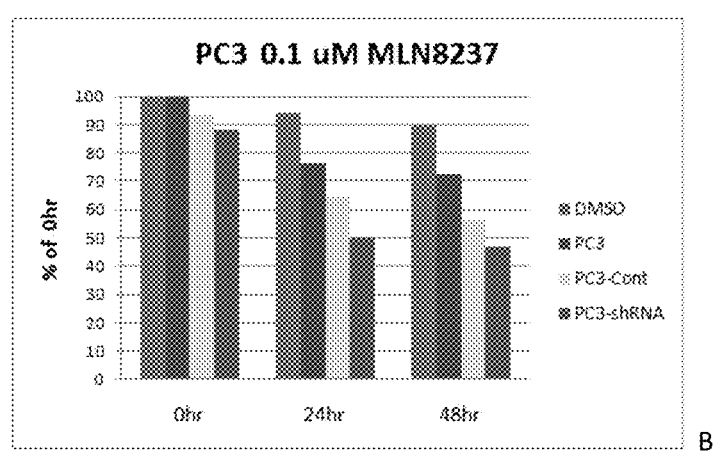
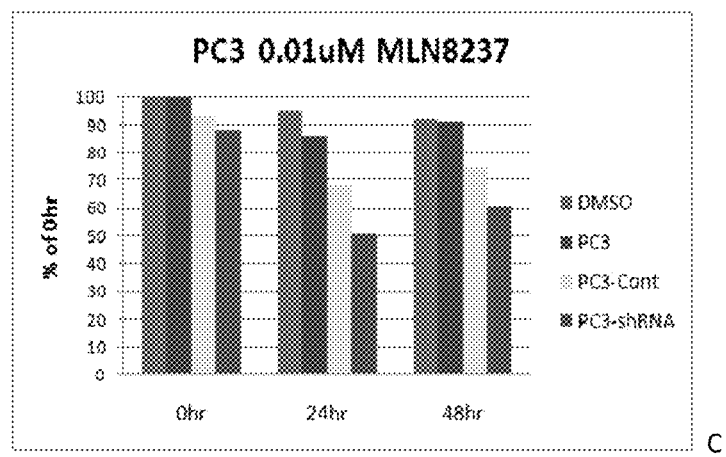
FIG. 10

SEQUENCE LISTING

```
<160> NUMBER OF SEQ ID NOS: 1

<210> SEQ ID NO 1
<211> LENGTH: 29
<212> TYPE: DNA
<213> ORGANISM: Unknown
<220> FEATURE:
<223> OTHER INFORMATION: Description of Unknown: LIMK1 oligonucleotide

<400> SEQUENCE: 1
aaggacaaga ggctcaactt catcactga                                    29
```

CO-TARGETING OF AURORA A KINASE AND LIM KINASE 1 FOR CANCER THERAPY

CROSS-REFERENCE TO RELATED APPLICATIONS

This application claims is related to U.S. Provisional Application No. 61/357,652; filed Jun. 23, 2010. Priority to this application is claimed under 35 USC 119 and is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 23, 2011, is named 10669079.txt and is 505 bytes in size.

BACKGROUND

Despite recent advances in development of improved cancer therapeutics one of the many clinical challenges is that patients often show resistance to cancer drugs. This invention provides evidence that an alternate method of treatment of cancer could be adopted for improved efficacy of existing therapies and/or treatment of drug resistant cancers. This study describes a novel functional relationship between two proteins that regulate proliferation of cells. Because these proteins are involved in cell growth, the amounts of these proteins are tightly regulated in normal cells however in cancer cells, abnormally increased amounts of these proteins are noted. One of the common methods for controlling abnormal growth of cancer cells is to inhibit production of these proteins. However, there are incidences of frequent development of resistance to the chemotherapeutic agents upon prolonged treatment, which sometimes is necessary to destroy all the cancer cells in the body.

Aurora A kinase (AurKA), a serine/threonine kinase and a member of Aurora kinase family, plays an essential role in proper mitotic function. Full activation of AurKA requires binding to the LIM domain containing protein. Earlier studies have indicated a possible role of a LIM domain containing serine/threonine and tyrosine kinase, LIM kinase 1 (LIMK1), in the mitotic process.

BRIEF DESCRIPTION OF THE DRAWINGS

FIG. 2 shows a diagram of Full length (LIMK), constitutively active phosphomimic (LIMKCA), LIM-domain only (LIMKLD), and kinase-domain only (LIMKKD) LIMK1 constructs.

FIG. 9 pertains to graphs presenting evidencing showing that LIMK1 inhibition potentiates the sensitivity of cells to an AurKA inhibitor.

FIG. 10 pertains to graphs presenting additional evidencing showing that LIMK1 inhibition potentiates the sensitivity of cells to an AurKA inhibitor.

DETAILED DESCRIPTION

Figure 1:
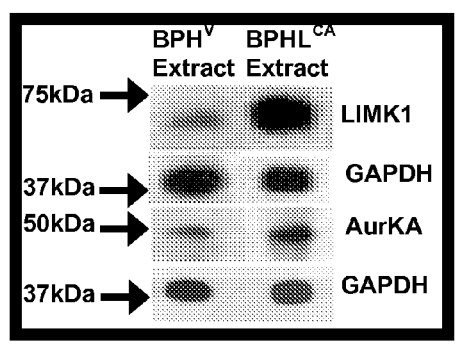
FIG. 1 shows a Western blot analysis showing expression of AurKA and LIMK1 in BPH and BPHL cells.

Disclosed herein are inventive embodiments that are based on the discovery that inhibition of LIMK1 in conjunction AurKA inhibitors potentiates the sensitivity of cells to the AurKA inhibitors. Accordingly, administration of an AurKA inhibitor together with LIMK1 inhibition will enable the use of lesser amounts of individual inhibitor while obtaining the same effect. Further, this will minimize the side effects of individual drugs and possibly delay the process of development of drug-resistant cancers.

Presented herein is evidence demonstrating a novel functional association between AurKA and LIMK1 in cancer cells, e.g., in prostate cancer cells. Overexpression of LIMK1 in benign prostate hyperplasia (BPH-1) cells resulted in increased expression of AurKA. Immunofluorescence analysis showed colocalization of phosphorylated LIMK1 with AurKA to the centrosomes in PC3 prostate cancer cells, which naturally overexpress LIMK1. shRNA mediated knockdown of LIMK1 decreased the level of phosphorylated AurKA and caused disorganized spindle morphology with phosphorylated AurKA localized to multiple spindle poles. Immunoprecipitation and pull-down assays showed that LIMK1 and AurKA associate in a complex. Interaction assays using deletion mutants of LIMK1 showed that AurKA binds to the LIM domains and the kinase domain independently in addition to the full-length LIMK1. LIMK1 acts as a substrate of AurKA and inhibition of AurKA activity resulted in mislocalization of phosphoLIMK1 and the centrosomal protein centrin.

The present disclosure indicates for the first time that AurKA and LIMK1 are functionally cooperating during mitosis. Overexpression of AurKA has been noted in a variety of cancers including prostate cancer and currently, small molecule inhibitors targeting AurKA are undergoing clinical trials. This study provides evidence that targeted inhibition of LIMK1 has the added benefit of functional inhibition of AurKA.

Aurora kinase A inhibitors are currently undergoing phase I and II clinical trials for cancer treatment but not all patients respond to this drug as resistance to kinase inhibitors develops frequently. The results of the evidence herein also provides evidence that targeted inhibition of Aurora A kinase may have the added benefit of also inhibiting LIMK1, and vice versa.

Accordingly, A) combination therapy of AurKA and LIMK1 inhibitors will improve effectiveness of AurKA inhibitors and B) inhibitors of LIMK1 function may be used for patients showing resistance to AurKA inhibitors. Furthermore, other inventive embodiments relate to the development of inhibitors of LIMK1 and use for combination therapy with AurKA inhibitors or use singly for AurKA resistant cancers.

In one embodiment, a single interfering RNA targeting LIMk1 or AurKA mRNA is administered to decrease respective levels of each. In other embodiments, two or more interfering RNAs targeting the LIMK1 and/or AurKA mRNA are administered to decrease LIMK1 and/or AurKA levels. In certain embodiments, interfering RNA targeting LIMK1 and/or interfering RNA targeting AurKA are administered to the subject sequentially or concurrently, thereby treating a related cancer.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-related cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

The GenBank database provides the DNA sequence for LIMK1 as accession no. NM_002314. Equivalents of the above cited LIMk1 mRNA sequence are alternative splice forms, allelic forms, isozymes, or a cognate thereof. A cognate is a LIMK1 mRNA from another mammalian species that is homologous to the cited human form (i.e., an ortholog).

The GenBank database provides the DNA sequence for AurKA as accession no NM_19843. Equivalents of the above cited AurKA mRNA sequence are alternative splice forms, allelic forms, isozymes, or a cognate thereof. A cognate AurKA mRNA from another mammalian species that is homologous to the cited human form.

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-related changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of the LIMK1 mRNA or AurKA mRNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

In certain embodiments, interfering RNA target sequences (e.g., siRNA target sequences) within a target mRNA sequence are selected using available design tools. Interfering RNAs corresponding to a LIMK1 or AurKA target sequence are then tested in vitro by transfection of cells expressing the target mRNA followed by assessment of knockdown as described herein. The interfering RNAs can be further evaluated in vivo using animal models as described herein.

Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

In a specific embodiment, the interfering RNA targeting LIMK1 is AAGGACAAGAGGCTCAACTTCATCACTGA (SEQ ID NO. 1)

It has been discovered that Aurora A induces phosphorylation of LIMK1 at T508 and Aurora A kinase and LIMK1 colocalize to the centrosomes. LIMK1 also phosphorylates AurKA and knockdown of LIMK1 reduces the level of phosphorylated Aurora A. Knockdown of LIMK1 further causes mislocalization of Aurora A kinase and disorganized spindle structure. The inventors work shows that Aurora A kinase and LIMK1 are functionally cooperative during mitosis.

As used herein, the term "effective amount" refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "therapeutic agent" refers to any molecule, compound, and/or substance that is used for the purpose of treating and/or managing cancer. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), antibody conjugates or antibody fragment conjugates, peptides (e.g., peptide receptors, selectins), binding proteins, chemospecific agents, chemotoxic agents (e.g., anti-cancer agents), radiation, chemotherapy, anti-angiogenic agents, and small molecule drugs. Therapeutic agents may be a(n) anti-angiogenesis therapy, targeted therapy, radioimmunotherapy, small molecule therapy, biologic therapy, epigenetic therapy, toxin therapy, differentiation therapy, pro-drug activating enzyme therapy, antibody therapy, chemotherapy, radiation therapy, hormonal therapy, immunotherapy, or protein therapy.

As used herein, the terms "therapies" and "therapy" can refer to any method(s), composition(s), and/or agent(s) that can be used in the treatment of a cancer or one or more symptoms thereof. In certain embodiments, the terms "therapy" and "therapies" refer to chemotherapy, radiation therapy, radioimmunotherapy, hormonal therapy, targeted therapy, toxin therapy, pro-drug activating enzyme therapy, protein therapy, antibody therapy, small molecule therapy, epigenetic therapy, demethylation therapy, histone deacetylase inhibitor therapy, differentiation therapy, antiangiogenic therapy, biological therapy including immunotherapy and/or other therapies useful in the treatment of a cancer or one or more symptoms thereof.

As used herein, the terms "treat", "treatment", and "treating" in the context of the administration of a therapy to a subject refer to the reduction or inhibition of the progression and/or duration of cancer, the reduction or amelioration of the severity of cancer, and/or the amelioration of one or more symptoms thereof resulting from the administration of one or more therapies. In a specific embodiment, a patient that is at a high risk for developing cancer is treated, i.e., a patient that has been diagnosed with a AurKa or Limk1 positive precancerous lesion. In specific embodiments, such terms refer to one, two, or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The present invention also provides methods for treating cancer, the methods comprising administering to a patient (e.g., a human patient) in need thereof, a therapeutically effective regimen, the regimen comprising administering to the patient an inhibitor of LIMK1 and an inhibitor of AurKA, or an inhibitor that inhibits both LIMK1 and AurKA, and optionally one or more additional therapies, said additional therapy not being compounds of the invention. The compound of the invention and the additional therapy can be administered separately, concurrently, or sequentially. The combination of agents can act additively or synergistically. PCT/US10/35800; filed May 21, 2010 is cited herein in its entirety, and specifically for a teaching of the many additional therapies that may be administered in conjunction with LIMK1 and/or AurKA inhibitors, or LIMK1/AurKA inhibitors. U.S. Patent Publication 20100144783 is cited to for examples of known AurKA inhibitors, as well as an exposition on the number of cancers that may be treated according to the compounds and methods of the invention. U.S. Patent Publication 20100120771 is cited for AurKA inhibitors. Macdonald et al. Mol Cancer Ther, 7:3490 (2008) is cited for teaching of LIMK1 inhibitors and methodology for indentifying such inhibitors, and U.S. App No. 12/706,218 is cited for teachings of LIMK1 inhibitors.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 1000 mg, conveniently administered, e.g. in divided doses up to four times a day or in retard form. Suitable unit dosage forms for oral administration comprise from ca. 1 to 1000 mg active ingredient. In view of the inventor's discovery that LIMK1 and AurKA inhibitors can work together synergistically, this will allow dosages of each to be administered at lower levels than that required for usage of only one or the other classes of inhibitors. Synergy refers to the additive effect of using a dose of another inhibitor that is not achieved by using the same dose of the same inhibitor. This is believed to lessen the possible toxicity that may be experienced with higher doses of a certain inhibitor. For example, if 100 mg is a determined daily dosage for only a AurKA inhibitor, then only 45 mg daily dosage of the AurKA inhibitor may be needed when 45-50 mg of a LIMK1 inhibitor is administered in combination to achieve the same treatment effect.

Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

In addition to the active ingredients, these pharmaceutical compositions can contain suitable pharmaceutically acceptable carriers comprising excipients and auxiliaries which facilitate processing of the active compounds into preparations which can be used pharmaceutically.

Pharmaceutical compositions comprising a compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragacanth, methylcellulose, sodium carboxymethylcellulose and/or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

EXAMPLES

Example 1

FIG. 1 Western blot analysis of the total cell extracts from BPHV or BPHLCA cells using anti-LIMK1 or anti-AurKA antibodies. GAPDH expression was used as the loading control. BPHLCA pertains to BPH-1 cells expressing Flag-tagged phosphomimic LIMK1 (constitutively active), BPHV pertains to cellsBPH-1 cells transfected with the empty vector. Cells expressing the LIMK1 phosphomic exhibited greater AurKA expression.

Example 2

FIG. 2 shows diagrams of full length (LIMK), constitutively active phosphomimic (LIMKCA), LIM-domain only (LIMKLD), and kinase-domain only (LIMKKD) LIMK1 constructs. These constructs were cloned into the pCMV14 vector used for expression in RWPE1 cells.

Example 3

Figure 3A:
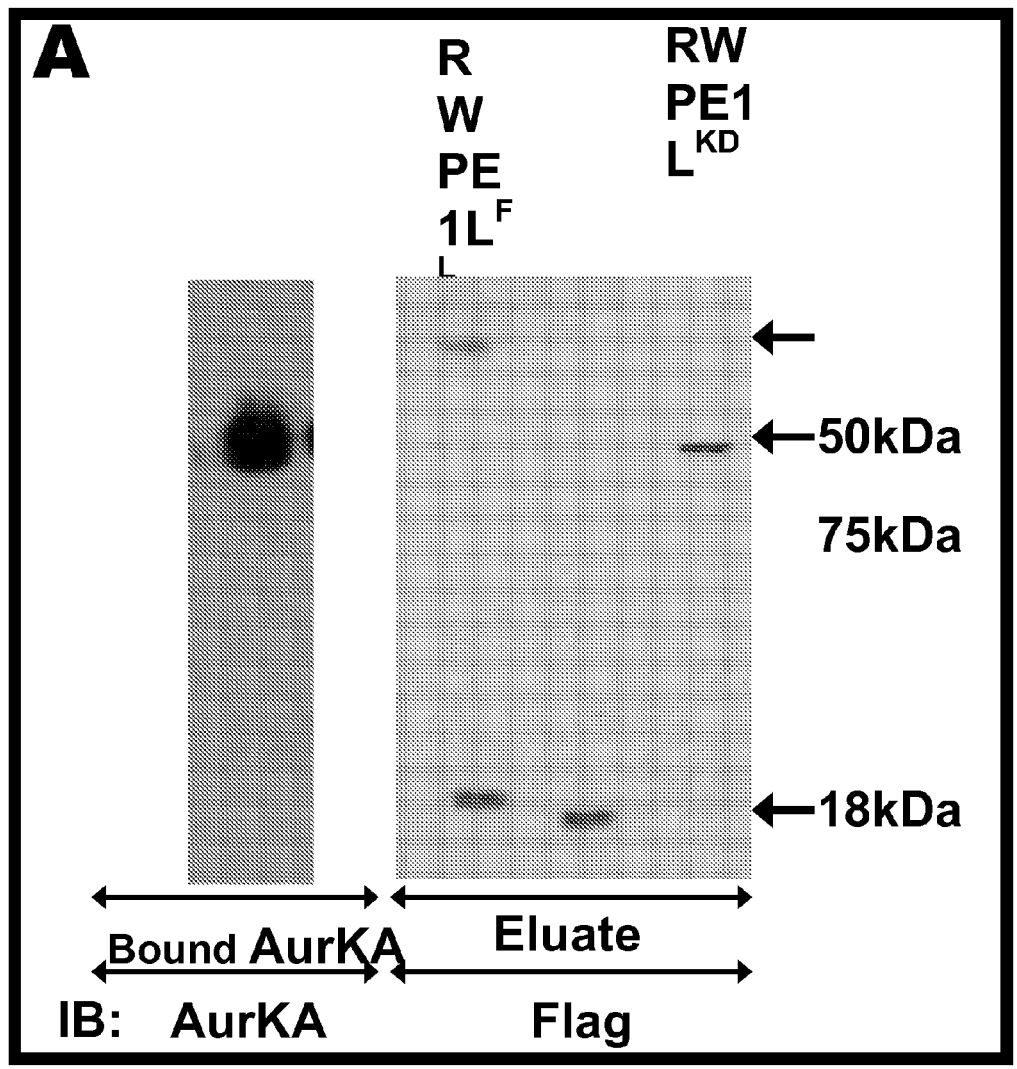
FIG. 3 A: shows results of a Pull-down assay demonstrating an association between LIMK and Aurora A.
FIG. 3B: shows western blot results demonstrating that Aurora A interacts with LIMK1 in vivo.
Figure 3B:
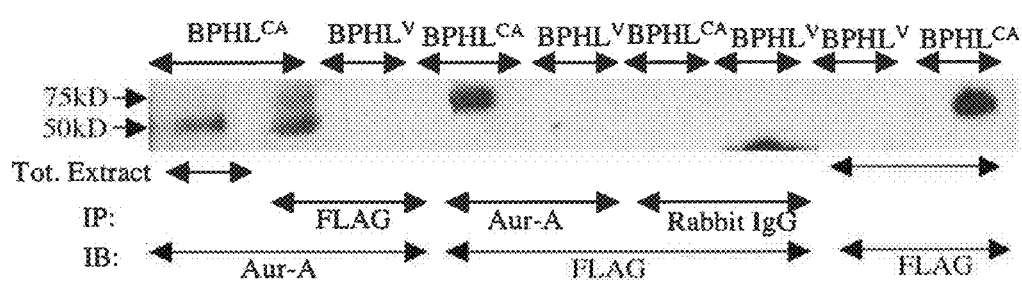

FIG. 3A shows the results of a Pull-down assay. Whole cell lysates from RWPE-1 cells transiently transfected with LIMK (RWPE1L), LIMKLD (RWPE1LLD), or LIMKKD (RWPE1LKD) were incubated with recombinant His-tagged Aurora A bound to magnetic His-bind beads. Pull-down of LIMK1 was detected by western blotting using anti-Flag antibodies. FIG. 3B shows that Aurora A interacts with LIMK1 in vivo. FIG. 3B provides western blots of AurKA or Flag-tagged LIMK1 in total cell extracts (Tot. extracts), FLAG immunoprecipitates, AurKA immunoprecipitates and rabbit IgG immunoprecipitates of total cell extracts prepared from BPHLCA and BPHV cells. An association between AurKA and LIMK1 is demonstrated in these western blots.

Example 4

Figure 4A:
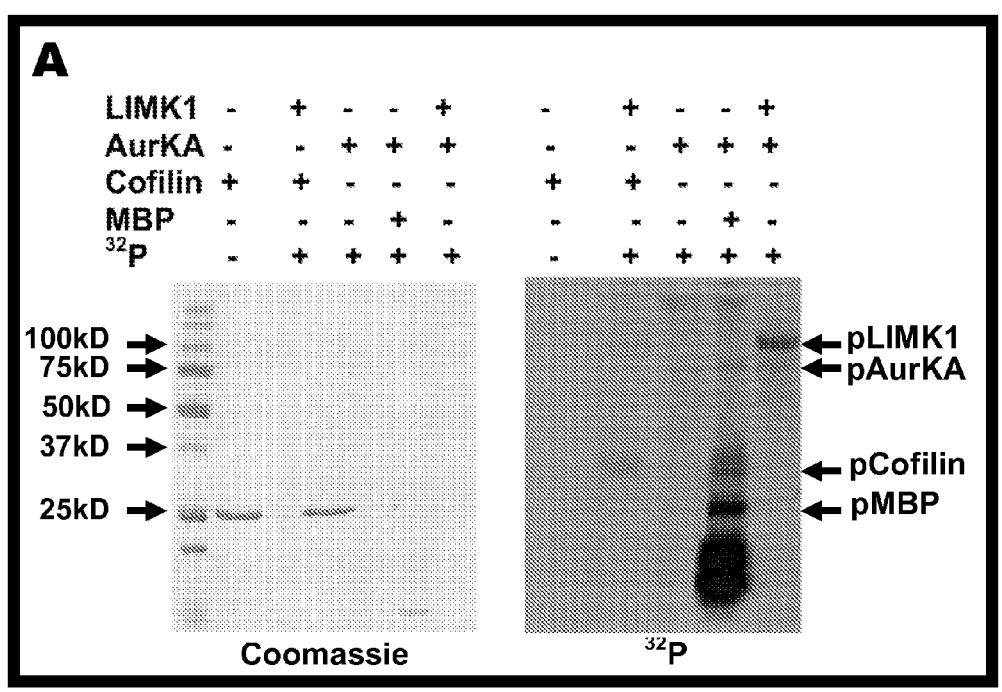
FIG. 4 A: shows results of in vitro kinase assays demonstrating Aurora A phosphorylates inactive LIMK1 in vitro.
FIG. 4B shows that incubation of Aurora A with LIMK1 resulted in phosphorylation of LIMK1 at T508.
Figure 4B:
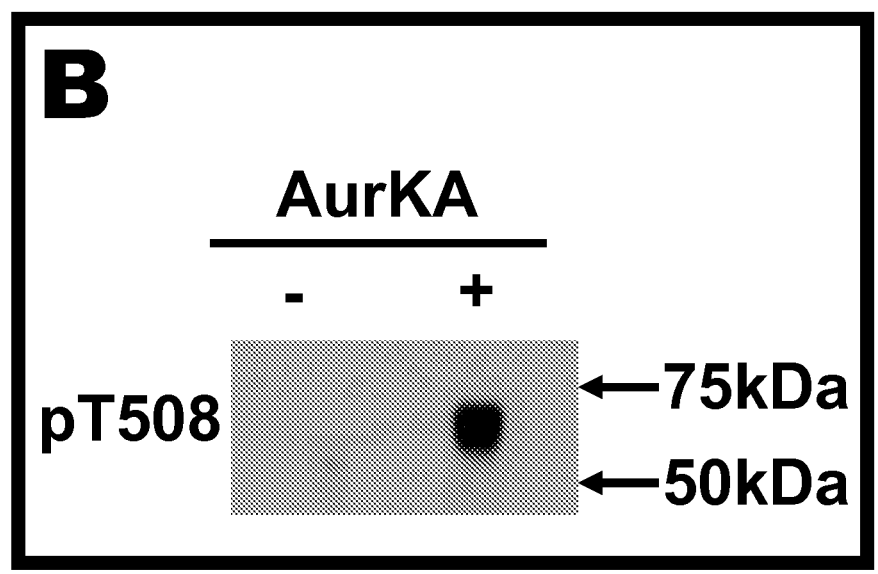

FIG. 4 shows that Aurora A phosphorylates inactive LIMK1 in vitro. In vitro kinase assays were performed using recombinant GST-Aurora A kinase and GST-LIMK1. 32P incorporation was detected by autoradiography. B: Incubation of Aurora A with LIMK1 resulted in phosphorylation of LIMK1 at T508. Whole cell extracts from RWPE-1 cells transiently expressing LIMK1 was treated with phosphatase and LIMK1 was immunoprecipitated using anti-Flag antibodies. Precipitates were then incubated in kinase assay buffer and cold ATP with or without recombinant AurKA. Phosphorylation at T508 was detected by western blotting using phospho-specific LIMK1 (T508) antibodies.

Example 5

Figure 5:
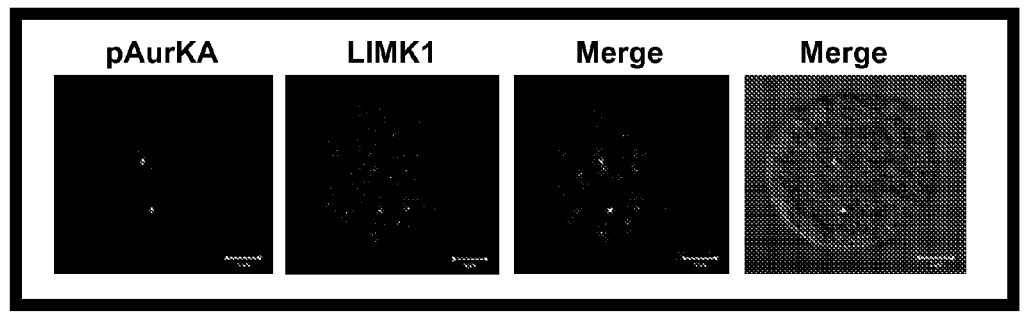
FIG. 5 Dual label immunofluorescence analysis shows that LIMK1 (red) and phospho AurKA (pAurKA) (green) colocalize to the centrosomes, which suggests their functional cooperativity FIG. 6 PC3 cells were transfected with LIMK1 shRNA or control shRNA and the levels of LIMK1 and pAurKA were detected by western blotting using anti-LIMK1 or anti phospho-AurKA antibodies. GAPDH was used as the loading control. The ratio of pAurKA to GAPDH levels was determined by densitometry (left panel).

FIG. 5 Dual label immunofluorescence analysis shows that LIMK1 (red) and phospho AurKA (pAurKA) (green) colocalize to the centrosomes. This suggests that these two enzymes possess functional cooperativity with eachother.

Example 6

Figure 6A:
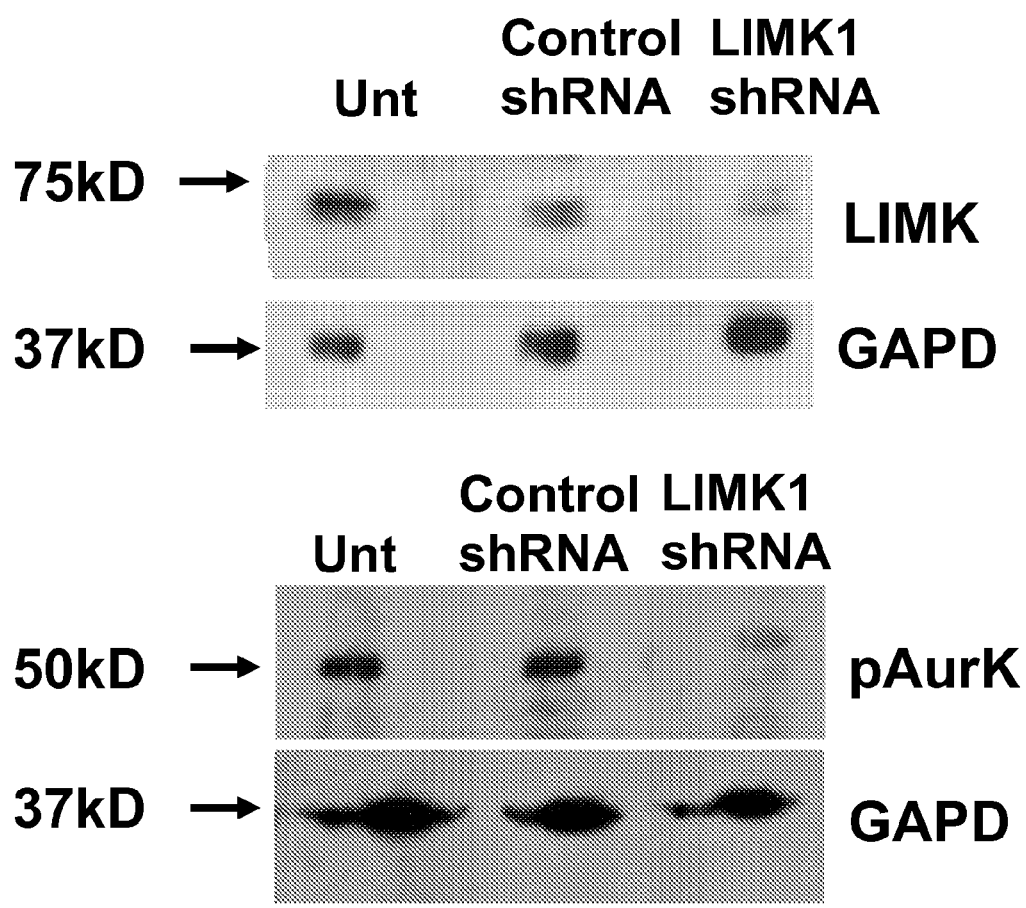
Figure 6B:
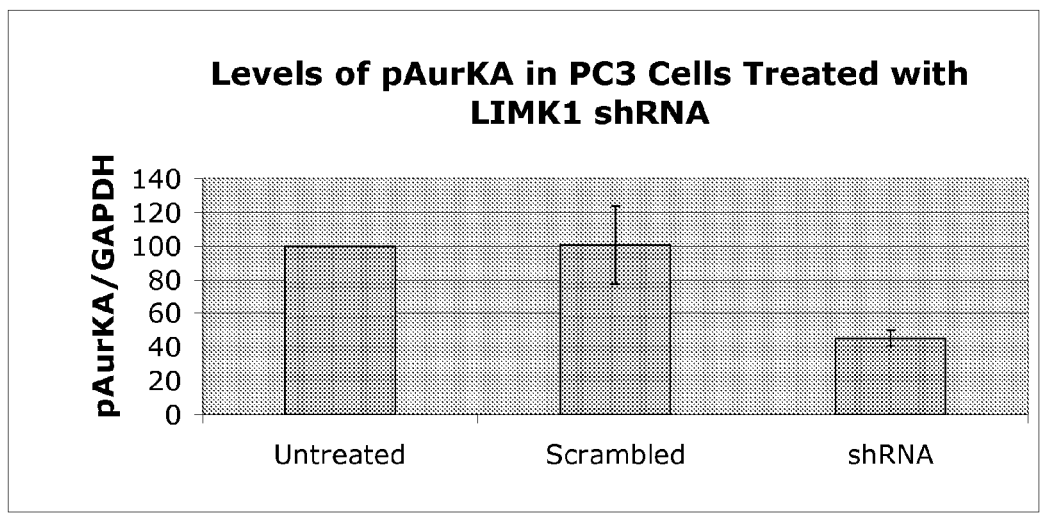

FIG. 6 PC3 cells were transfected with LIMK1 shRNA or control shRNA and the levels of LIMK1 and pAurKA were detected by western blotting using anti-LIMK1 or anti phospho-AurKA antibodies. GAPDH was used as the loading control. The ratio of pAurKA to GAPDH levels was determined by densitometry (left panel).

Example 7

Figure 7A:
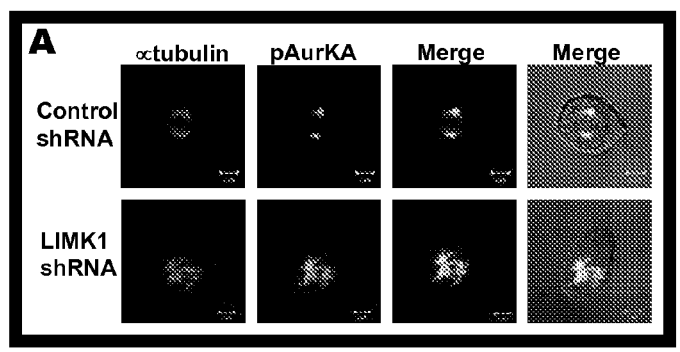
FIG. 7 A: PC3 cells were transfected with either LIMK1 or control shRNA. In control shRNA transfected cells, distinct localization of pAurKA (green) at the spindle poles (red) could be noted. In LIMK1 shRNA treated cells, alpha-tubulin staining (red) showed disorganized spindle structure.
FIG. 7B: Knockdown of LIMK1 increased the number of abnormal spindles in PC3 cells. PC3 cells were transfected with either LIMK1 or control shRNA and spindle abnormalities were quantified by counting 50 cells per treatment.
Figure 7B:
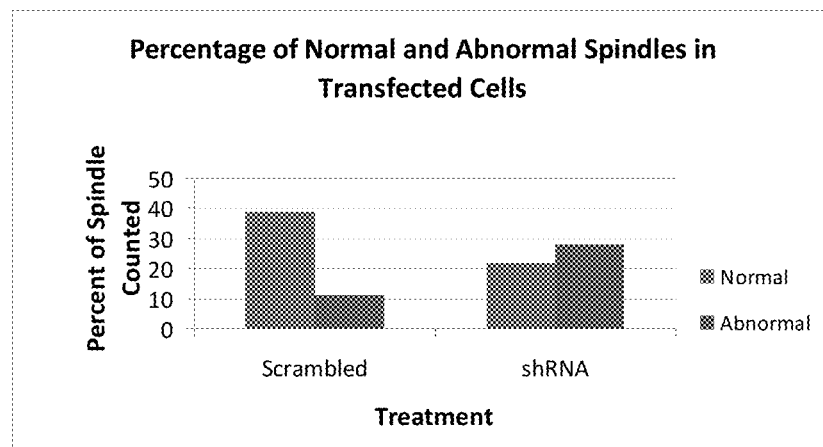

FIG. 7 A: PC3 cells were transfected with either LIMK1 or control shRNA. In control shRNA transfected cells, distinct localization of pAurKA (green) at the spindle poles (red) could be noted. In LIMK1 shRNA treated cells, alpha-tubulin staining (red) showed disorganized spindle structure. Diffused B: Knockdown of LIMK1 increased the number of abnormal spindles in PC3 cells. PC3 cells were transfected with either LIMK1 or control shRNA and spindle abnormalities were quantified by counting 50 cells per treatment.

Example 8

Figure 8A:
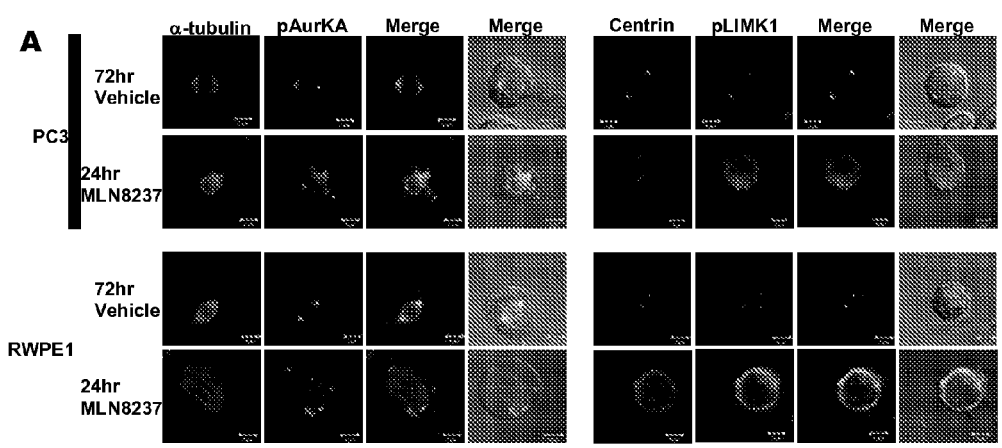
FIG. 8. Treatment with Aurora A kinase inhibitor MLN8237 resulted in Mislocaliation of phosphoLIMK1 and phosphoAurK A: PC3 and RWPE1 cells were treated with MLN8237 (0.01 uM) for 24 hr or the vehicle (DMSO) for 72 hr. Immunofluorescence analysis showed that treatment with MLN8237 caused mislocalization of pAurKA (green) and improper spindle morphology (alpha-tubulin) (red). In addition, diffused staining and mislocalization of pLIMK1 (green) and centrin (red) in the nucleus were noted. The vehicle control cells showed colocalization of pLIMK1 with centrin to the centrosomes (red). Aurora A Inhibition Increased the Levels of phospho-Histone H3 suggesting mitotic arrest (B). Western blot analysis of nuclear extracts from PC3 cells treated with MLN8237 (0.01 uM). 1-tubulin staining was used as the loading control. Aurora A Inhibition Decreased Cell Survival (C). PC3 and RWPE1 cells were treated with MLN8237 (0.01 uM) MLN8237 for 24, 48, and 72 hr and cell viability was measured by MTT Assay.
Figure 8B:
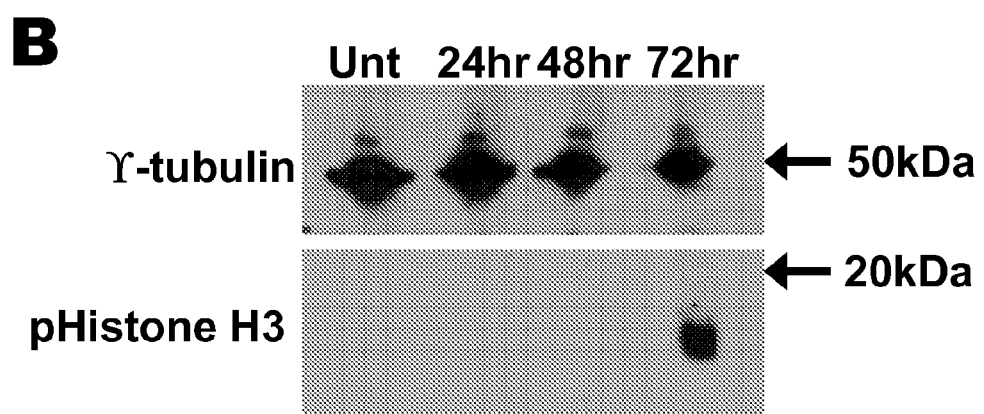
Figure 8C:
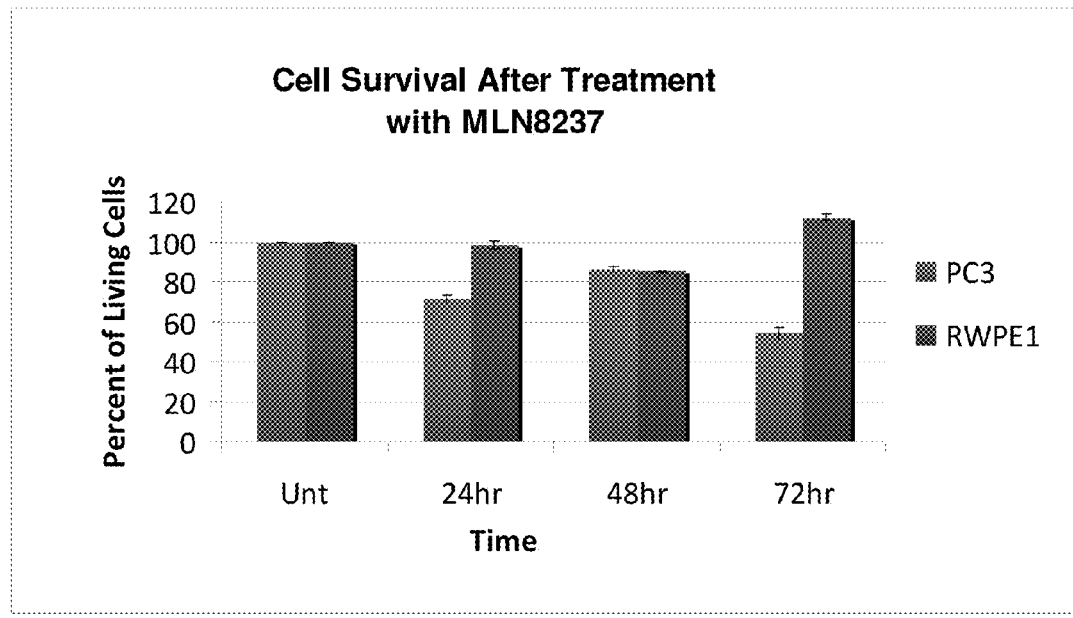

FIG. 8. Treatment with Aurora A kinase inhibitor MLN8237 resulted in Mislocaliation of phosphoLIMK1 and phosphoAurK A: PC3 and RWPE1 cells were treated with MLN8237 (0.01 uM) for 24 hr or the vehicle (DMSO) for 72 hr. Immunofluorescence analysis showed that treatment with MLN8237 caused mislocalization of pAurKA (green) and improper spindle morphology (alpha-tubulin) (red). In addition, diffused staining and mislocalization of pLIMK1 (green) and centrin (red) in the nucleus were noted. The vehicle control cells showed colocalization of pLIMK1 with centrin to the centrosomes (red). Aurora A Inhibition Increased the Levels of phospho-Histone H3 suggesting mitotic arrest (B). Western blot analysis of nuclear extracts from PC3 cells treated with MLN8237 (0.01 uM). Y-tubulin staining was used as the loading control. Aurora A Inhibition Decreased Cell Survival (C). PC3 and RWPE1 cells were treated with MLN8237 (0.01 uM) MLN8237 for 24, 48, and 72 hr and cell viability was measured by MTT Assay.

Example 9

Inhibition of LIMK1 has a synergistic effect on treatment with AurKA inhibitor MLN8237

Experimental Procedure:

10 cm dishes were transiently transfected with 6 ug of LIMK1 shRNA or control shRNA. 24 hrs post transfection, untransfected PC3 cells along with the transfected PC3 cells were seeded in 96 well plates in triplicate (5,000 cells/well). 14 hrs after seeding, media was changed to MLN8237 containing media, at concentrations of 0.001 uM, 0.01 uM, and 0.1 uM. After 24 and 48 hours of inhibitor treatment, cell proliferation was measured using MTS assay. MTS reagent was added to each well and allowed to incubate for 3 hrs at 37° C. before reading absorbances. Absorbances were compared against controls.

Figure 11:
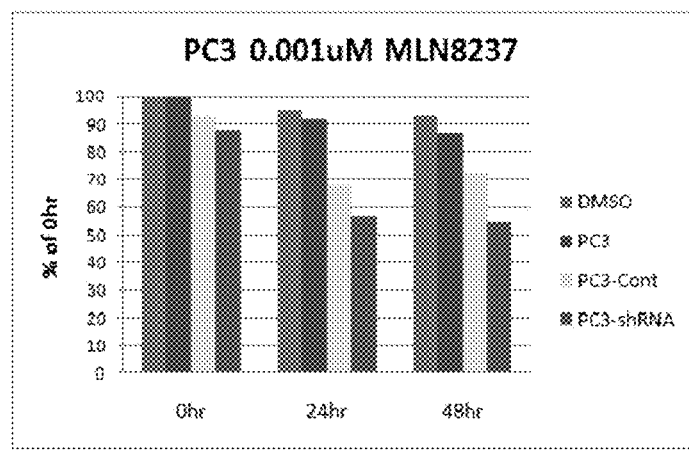
FIG. 11 pertains to graphs presenting further evidencing showing that LIMK1 inhibition potentiates the sensitivity of cells to an AurKA inhibitor.

Results:

Results for this example are shown in FIGS. 9-11. Untransfected PC3 cells were most sensitive to 0.1 uM MLN8237 at 48 hrs. Inhibition seemed to be linear and increased with time. Untransfected PC3 cells were less sensitive than the transfected cells.

PC3 cells transfected with LIMK1 shRNA experienced more sensitivity to MLN8237 than those cells transfected with the control shRNA. The number of viable cells in both transfected samples decreased with time and concentration of MLN8237, although the relative difference in viable cells between the control and LIMK1 shRNA was not consistent with concentration of inhibitor. LIMK1 knockdown appeared to increase sensitivity at lower inhibitor concentrations.

At 48 hrs: 0.001 uM treatment resulted in LIMK1 knockdown wells having only 75% of the number of viable cells compared to control shRNA. While in the 0.1 uM treatment, LIMK1 knockdown wells had 83% of the number of viable cells compared to the control shRNA.

When compared with untransfected PC3 cells treated with the vehicle (DMSO) LIMK1 knockdown increased the sensitivity of the cells to AurKA inhibitor at all concentrations at both 24 and 48 hr of treatment compared to untranfected PC3 cells only treated with AurKA inhibitor.

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method for treating prostate cancer in a subject, said method comprising administering a therapeutically effective amount of a LIM kinase 1 (LIMK1) inhibitor and an Aurora Kinase A (AurKA) inhibitor to said subject, wherein said LIMK1 inhibitor comprises an antibody that binds to LIMK1, and the AurKA inhibitor comprises MLN8237 or an antibody that binds to AurKA.

2. The method of claim 1, wherein said LIMK1 inhibitor is an antibody that bind to LIMK1 and said AurKA inhibitor is an antibody that binds to AurKA.

3. The method of claim 1, further comprising administering an additional therapy to said subject prior to, during or subsequent to said administering of said LIMK1 and AurKA inhibitors.

4. The method of claim 1, wherein said therapeutically effective amount of a LIMK1 inhibitor and a AurKA inhibitor comprises a dosage of each that is effective for treatment of the cancer and which is lower than a dosage required to achieve the same level of treatment with only one of the inhibitors.

* * * * *